United States Patent [19]

Maeda et al.

[11] Patent Number: 5,087,614
[45] Date of Patent: Feb. 11, 1992

[54] ENZYME INHIBITOR AND METHOD OF PRODUCING THE SAME

[75] Inventors: Mitsuru Maeda, Shiga; Tohru Kodama, Osaka; Norio Iwasawa, Osaka; Naoki Higuchi, Osaka; Norihide Amano, Osaka, all of Japan

[73] Assignee: Suntory Limited, Osaka, Japan

[21] Appl. No.: 271,965

[22] Filed: Nov. 16, 1988

[30] Foreign Application Priority Data

Nov. 17, 1987 [JP] Japan .................... 62-289995

[51] Int. Cl.$^5$ .............................................. A61K 37/02
[52] U.S. Cl. .......................... 514/16; 514/17; 514/18; 514/19; 530/329; 530/330; 530/328; 435/128; 435/135; 435/142; 435/826
[58] Field of Search .......... 530/329, 330, 328; 514/18, 19, 17, 16

[56] References Cited

U.S. PATENT DOCUMENTS 4,479,941 10/1984 Veber et al. ...................... 514/18
4,735,933 4/1988 Hudspeth et al. .................. 514/18
4,874,745 10/1989 Huang et al. ..................... 514/18

FOREIGN PATENT DOCUMENTS 0040435 11/1981 European Pat. Off. .
0184855 6/1986 European Pat. Off. .

OTHER PUBLICATIONS

Pepstatin, A New Pepsin Inhibitor Produced by Actinomycetes, The Journal of Antibiotics, vol. XXIII No. 5, pp. 259–263.
European Search Report dated May 10, 1990, in Application No. EP 88 11 9126.
Kakinuma & Kanamaru, J. Takeda Res. Lab. 35(3/4):123–127 (1976).
Umezawa et al., J. Antibiotics, 23(5):259–262 (1970).
Aoyagi, et al., J. Antibiotics, 26(9):539–541 (1973).
Umezawa, et al., J. Antibiotics, 26(10):615–617 (1973).
Miyano, et al., J. Antibiotics, 25(8):489–491 (1972).
Murano & Satori, Agr. Biol. Chem., 34(8):1265–1267 (1970).
Takahashi, et al., J. Gen. Appl. Microbiol., 30:377–387 (1984).
Omura, et al., J. Antibiotics, 35(8):1013–1019 (1982).
Iwami, et al., J. Antibiotics, 40(5):612–622 (1987).

Primary Examiner—Glennon H. Hollrah
Assistant Examiner—John D. Pak
Attorney, Agent, or Firm—Cushman, Darby & Cushman

[57] ABSTRACT

Novel peptide analogues which exhibit inhibitory activity against aspartic proteinases, a novel species of actinomycetous microorganism which produces said novel peptide analogues, a process for producing said novel analogues by culturing said species and a pharmaceutical composition containing said analogues.

2 Claims, 6 Drawing Sheets

ENZYME INHIBITOR AND METHOD OF PRODUCING THE SAME

FIELD OF THE INVENTION

The present invention relates to novel biologically active compounds which exhibit an inhibitory activity against enzymes such as aspartic proteinases, e.g., pepsin, renin and the like, as well as to a microorganism of the genus Kitasatosporia having the ability to produce said compounds, and a method of producing the compound using the microorganism.

Representatives of aspartic proteinase which is known to exist in living organisms include pepsin, which is found in the stomach, renin, which is found in the liver, and so forth. Pepstatin (Umezawa et al., J. Antibiotics, 23, 259 (1970) or Japanese Patent Laid-Open 29582/1972) and pepstanone (Miyano et al., J. Antibiotics, 25, 489 (1972) or Japanese Patent Laid-Open No. 88281/1973) are well known as low-molecular weight peptide inhibitors which act on such aspartic proteinase. Examples of pepstatin analogues include hydroxypepstatin (Umezawa et al., J. Antibiotics, 27, 615 (1973)) in which the alanine residue is replaced by a serine residue and analogues in which the acyl group at the N-terminal is a straight chain group having 2 (acetic acid) to 20 (alginic acid) carbon atoms or a branched aliphatic group (isolated by Aoyagi et al., J. Antibiotics, 26, 539 (1973)). SP-1 (Murao et al, Agric. Biol. Chem., 34, 1265 (1970)) and pepsinostreptin (Kakinuma et al., J. Takeda Res. Lab., 35, 123 (1976)) are identical to the substances included in this classification of pepstatin compounds. All of such compounds are characterized by being pentapeptides in which the third residue from the N-terminal and the C-terminal contains an abnormal amino acid statin ((3S, 4S)-4-amino-3-hydroxy-6-methylheptanoic acid) or, in the case of pepstanone, the C-terminal contains stanone ((3S)-3-amino-5-methylhexane-2-one), and in which a straight or branched aclyl group is bonded to the N-terminal. Although many known low-molecular weight peptide inhibitors which act on aspartic proteinases are produced by microorganisms, these inhibitors are not readily dissolved in solvents because of the nature of their structures. Therefore, they cannot be easily purified and, in addition, the permeability of these inhibitors through biological systems is not particularly good. From this viewpoint, there is a demand for novel biologically active substances which not only have inhibitory activity against aspartic proteinases but also have good compatibility with solvents.

SUMMARY OF THE INVENTION

The object of the present invention is to provide novel biologically active compounds which exhibit inhibitory activity against aspartic proteinases such as pepsin, renin and the like.

A further object of the present invention is to provide novel statin analogues which have inhibitory activity against aspartic proteinases as well as good compatibility with various solvents such as methanol, ethanol, dimethyl sulfoxide and butanol etc., and hence can be expected to have good permeability through biological systems.

A still further object of the present invention is to provide *Kitasatosporia kyotoensis*, a novel actinomycetous species of the genus Kitasatosporia, which is capable of producing novel statin analogues having inhibitory activity against aspartic proteinases as well as having good compatibility with various solvents.

A yet further object of the present invention is to provide a method for producing novel statin analogues of the invention by cultivation of a strain of *Kitasatosporia Kyotoensis* followed by isolation and purification of said analogues from the culture medium.

Still another object of the invention is to provide a pharmaceutical composition which comprises at least one compound of the general formula I, together with a pharmaceutically acceptable carrier.

These and other objects of the invention will be apparent from the following description.

DETAILED DESCRIPTION OF THE INVENTION

Figure 1:
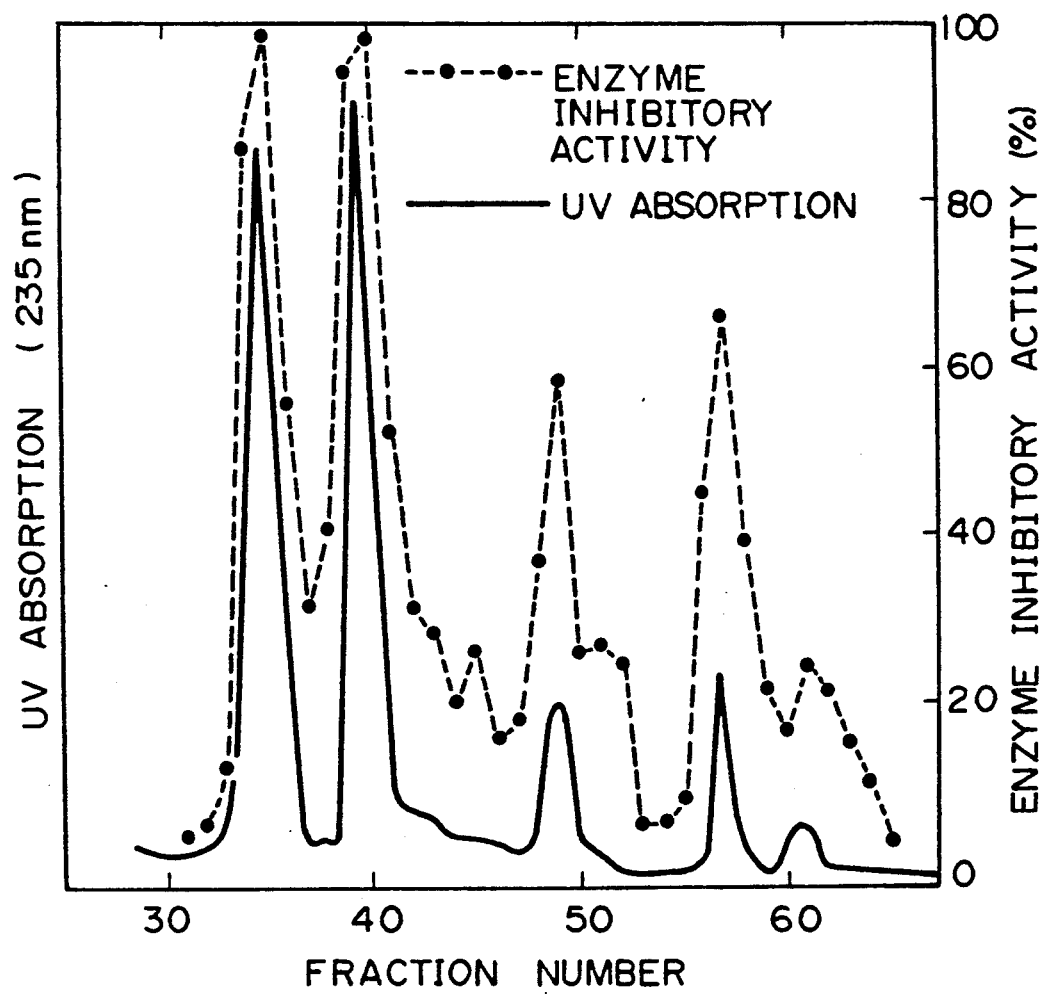
FIG. 1 is a graph of the elution pattern obtained by high performance liquid chromatography in the final stage of production of SUAM-20009 and SUAM-20010 in Example 1.

As a result of extensive investigations conducted by the inventors with a view to discovering a novel microorganism which is capable of producing biologically active compounds having a novel structure and exhibiting inhibitory activity against the enzyme function of aspartic proteinases, the inventors found that a group of biologically active compounds exhibiting such inhibition against various aspartic proteinases can be produced from a culture solution of *Kitasatosporia kyotoensis* strain SAM0107, which was isolated from a soil sample collected in Kyoto, Japan, and which belongs to actinomycetous microorganisms. The inventors also succeeded in isolating and purifying these biologically active compounds in a pure state. Such novel compounds of the present invention are significantly different from the known pepstatin analogues in terms of the number and arrangement of the amino acid residues and the acyl groups at the N-terminals.

The compounds of the present invention which have inhibitory activity against the enzyme function of aspartic proteinases have a structure represented by the general formula I:

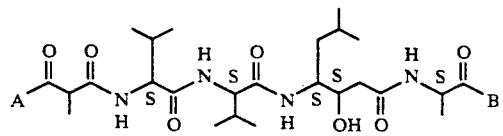

wherein A denotes —OH or —O—CH₃ and B denotes

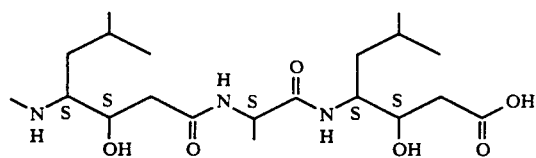

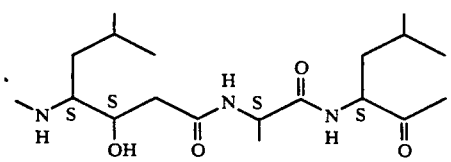

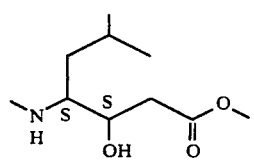

or

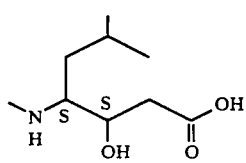

or

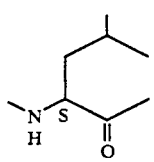

The *Kitasatosporia kyotoensis* SAM0107 which is a novel microorganism capable of producing the biologically active substances of the general formula I has the following morphology and cultural characteristics:

1) Morphological character

The SAM0107 strain forms a straight chain with a spiral end at the end of an aerial hypha which is not so long. The straight chain of mature spore comprises 20 to 50 or more spores. Each of the spores has a size of (0.4 to 0.8) μm×(0.8 to 1.2) μm and a smooth surface. No fragmentation is to be observed in substrate mycelium.

2) Cultural character (culture at 28° C. for 14 days)
  Sucrose-nitrate agar medium:
    Aerial mycelium; None
    Reverse side color; White to light yellow
    Soluble pigment; None;
  Glucose-asparagine agar medium:
    Aerial mycelium; Thin, white to grey
    Reverse side color; Yellowish brown
    Soluble pigment; None
  Glycerin-asparagine agar medium:
    Aerial mycelium; Thin, white to grey
    Reverse side color; Yellowish brown
    Soluble pigment; Brown
  Inorganic salts-starch agar medium:
    Aerial mycelium; Dense, white Reverse side color; Dark yellowish brown
  Soluble pigment; None
  Tyrosine agar medium:
    Aerial mycelium; Thin, white to grey
    Reverse side color; Brown
    Soluble pigment; Dark brown
  Nutrient agar medium:
    Aerial mycelium; None
    Reverse side color; Light yellow
    Soluble pigment; None
  Yeast extract-malt extract agar medium:
    Aerial mycelium; Dense, white to grey
    Reverse side color; Yellowish brown
    Soluble pigment; None
  Oatmeal agar medium:
    Aerial mycelium; Thin, white to grey
    Reverse side color; Yellowish brown
    Soluble pigment; None
  Peptone-yeast extract-iron agar medium:
    Aerial mycelium; None
    Reverse side color; Light yellow
    Soluble pigment; None 3) physiological property
  (1) Growth temperature range (culture in a CYC liquid medium for 3 days)
    Viable temperature: 18 to 31° C.
    Optimum growth temperature: 21 to 24.5° C.

| | |
|---|---|
| (2) Liquefaction of gelatin | Negative |
| (3) Hydrolysis of starch | Positive |
| (4) Coagulation of milk | Negative |
| (5) Peptonization of milk | Negative |
| (6) Production of melanoid pigment | |
| Peptone-yeast extract-iron agar medium | Negative |
| Tyrosine agar medium (0.2% glucose, 1.0% yeast extract (Difco), 0.05% L-tyrosine, 0.5% NaCl, 2.0% agar, pH 7.0 | Negative |
| Trypton-yeast extract agar medium | Negative |
| (7) Reduction of nitrate | Positive |

(8) Utilization of carbon source (culture in Pridham and Gottlieb medium at 28° C. for 14 days)

| | |
|---|---|
| D-glucose | + |
| D-xylose | + |
| L-arabinose | + |
| L-rhamnose | — |
| D-fructose | ± |
| D-galactose | + |
| Raffinose | — |
| D-mannitol | — |
| Inositol | — |
| Salicin | ± |
| Sucrose | + |

(+, utilized; ±, doubtful whether the carbon source is utilized or not; —, not utilized).

4) Chemical Properties (1) Cell Wall a. Amino Acid

As a result of examination of the hydrolysate of whole cells and the cell wall in accordance with the method of Stanek, J. L. and Roberts, G. D. (Applied Microbiology, 28, 226 (1974), the existence of two isomers, meso-2,6-diaminopimelic acid and L,L-2,6-diaminopimelic acid, as well as glycine was observed.

b. Sugar

Ribose, mannose, glucose and galactose exist in the hydrolysate of whole cells.

(2) Quinone System

It contains MK-9(H₆) and MK-9(H₈) as major components.

The morphology and cultural characteristics of this strain are summarized below.

Aerial hyphae of the SAM0107 strain are relatively short and have spore chains which are straight and have a spiral end. The spore chain comprises 20 to 50 or more spores. The surface of the spore is smooth. Aerial hyphae which are white to yellowish grey adhere to substrate hyphae which are light yellow to brown, in various mediums. Soluble pigments of dark brown are produced in tyrosine agar medium but no melanoid pigment is produced.

Meso-2,6-diaminopimelic acid, L,L-2,6-diaminopimelic acid, glycine, ribose, mannose, glucose and galactose were observed in the hydrolysate of whole cells. The quinone system has MK-9($H_6$) and MK-9($H_8$) as major components.

From the viewpoint described above, particularly the fact that two isomers of 2,6-diamminopimelic acid exist in the hydrolysate of whole cells, it can be concluded that the strain SAM0107 belongs to the genus Kitasatosporia (J. Antibiotics, 35, 1013 (1982); The Actinomycetologist (The society for Actinomycetes, Japan), 45, 12, 1984).

Examples of actinomycetes belonging to the genus Kitasatosporia include *Kitasatosporia setalba* KM-6054 reported by OMURA et al. in J. Antibiotics, 35, 1013 (1982); *Kitasatosporia phosalacinea* KA-338 and *Kitasatosporia griseola* AM-9660 reported by TAKAHASHI et al. in J. Gen. Appl. Microbiol., 30, 377 (1984); *Kitasatosporia melanogena* K-55-G-32 reported by SHIMAZU et al. on page 9 in the summary of the annual meeting of the Society for Actinomycetes Japan in Osaka, 1984; Kitasatosporia sp. SANK60684 reported by INAOKA et al in Japanese Patent Laid-Open No. 088884/1986; Kitasatosporia sp. RK-419 reported by ISONO et al. in Japanese Patent Laid-Open No. 146188/1986; *Kitasatosporia setae* MF730-N6 reported by UMEZAWA et al. in Japanese Patent Laid-Open No. 285992/1986; *Kitasatosporia kifnense* 9482 reported by IWAMI et al. in J. Antibiotics, 40, 612 (1987) and *Kitasatosporia clausa* 33.35-1 reported by Liu, Z. et al. in Acta Microbiologica Sinica, 26, 87 (1986).

As compared with these strains, the SAM0107 strain is clearly different from these strains in the fact that the SAM0107 strain forms spore chains having ends with a spiral form, while *Kitasatosporia setalba* KM-6054, *Kitasatosporia phosalacinea* KA-338, *Kitasatosporia griseola* KM-9660, *Kitasatosporia melanogena* K55-G-32 and *Kitasatosporia setae* MF-730-N6 displays spore chains having an end with a rectusflexibilis form and the spore chains of Kitasatosporia sp. SANK60684 have a straight or curved form.

Although the *Kitasatosporia kifnense* 9482 forms spore chains with ends having a hooked or spiral form, this strain is clearly distinguishable from the strain SAM0107 of the present invention with respect to the production of soluble pigments in a glycerin-asparagine agar medium, the reduction of a nitrate and the utilization of D-xylose and D-mannitol.

The Kitasatosporia sp. RK-419 forms spore chains having ends with an open spiral form but is clearly distinguished from the strain SAM0107 of the present invention with respect to the formation of aerial mycelium in a sucrose-nitrate agar medium, the production of soluble pigments in a glycerin-asparagine agar medium and in a tyrosine agar medium, the formation of aerial mycelium in a nutrient agar medium, growth in a peptone-yeast extract-iron agar medium, utilization of D-xylose, L-arabinose and raffinose, coagulation of milk, peptonization of milk and the sugar composition of the hydrolytic product of whole cells.

The *Kitasatosporia clausa* 33.35-1 is clearly distinguished from the strain SAM0107 with respect to the fact that the substrate hyphae are fragmented. In view of the above-described consideration, the inventors concluded that the strain SAM0107 belongs to a new species of the genus Kitasatosporia and named the species *Kitasatosporia kyotoensis*.

This strain was deposited at the Fermentation Research Institute, Agency of Industrial Science and Technology on Sept. 10, 1987, and given accession number FERM P-9580. The deposit was transferred to a deposit under the Budapest Treaty as of Sept. 9, 1988, and given accession number FERM BP-2045.

It can be inferred that the biologically active compounds of the present invention can be produced by a person skilled in the art using a known method of synthesizing peptides. Although the compounds synthesized by such synthetic methods are intended to be included in the present invention, the biologically active compound can be more conveniently produced on a commercial scale by culturing actinomycetous microorganisms belonging to the genus Kitasatosporia and having the ability to produce biologically active compounds of the formula I in an appropriate medium, followed by separation of the compounds from the culture medium and purification thereof.

The medium used for producing the biologically active compounds in the present invention may be either liquid or solid, but shaking culture or aerobic agitating culture in a liquid medium is generally convenient. Any medium which allows the growth of the microorganism producing the compounds of the present invention and accumulation of the product therein may also be used. In other word, for example, glucose, lactose, glycerin, starch, sucrose, dextrin, molasses and organic acids are used as carbon sources, and protein hydrolysate such as peptone and casamino acid, meat extract, yeast extract, soybean meal, corn steep liquor, amino acids, ammonium salts, nitrates and other organic and inorganic nitrogen compounds are used as nitrogen sources. Various phosphates, magnesium sulfate or sodium chloride may be added as an inorganic salt to the medium, and vitamins and compounds relevant to nucleic acids may be added thereto for the purpose of accelerating the growth of the microorganism. The addition of silicone, polypropylene glycol derivatives or soybean oil which all serve as an antifoamer to the medium is in some cases effective for increasing the amount of the compounds accumulated in the medium in accordance with the present invention.

Preferably, pre-culture on a small scale is first performed and the pre-cultured organisms are then inoculated in the medium rather than starting the production culture directly. Although the conditions such as the culture temperature, culture period and the properties of the culture solution are appropriately selected and adjusted so that the accumulation of the compounds of the invention will be the maximum possible, the culture in many cases is preferably performed at 25° C. to 35° C. for 1 to 3 days under aerobic conditions, with the pH value of the culture solution being kept at 4.0 to 9.5.

Such culture enables the compounds of the invention to be accumulated in the culture mixture. In the case of culture using a liquid medium, the desired compounds are mainly accumulated in the liquid portion, and it is hence preferable that the culture mixture is first filtered or centrifuged so that the microorganism is removed, and the desired compounds are then separated from the filtrate or supernatant. Alternatively, the compounds can also be isolated directly from the culture mixture without the microorganisms being removed. The compounds can be separated from the culture mixture and purified by using various methods based on the chemical characteristics of the compounds of the present invention. Examples of methods that may be effectively used include precipitation by addition of ammonium sulfate or the like; extraction with an organic solvent such as n-butanol which does not freely mix with water and which is capable of dissolving the compounds of the invention therein; dissolution in polar solvents such as methanol and ethanol; removal of impurities by treatment with hexane; gel filtration using a matrix of Sephadex types; ion exchange chromatography using various types of iron exchangers such as ion-exchange resin, ion-exchange cellulose and ion-exchange Sephadex; and adsorption chromatography using adsorbents such as activated charcoal, alumina, silica gel, Amberlite XAD-1 or 2. The compounds of the invention can be isolated in a white amorphous form by appropriately combining these methods. Any other methods which appropriately utilize the characteristics of the compounds of the invention may also be suitably used. Examples of particularly preferred adsorbents include Diaion HP-20, Sephadex LH-20, TSKG-3000S, Cosmosil 10C18 and DEAE-cellulose.

The biologically active compounds produced by the method of the present invention exhibit the ability to inhibit aspartic proteinases such as pepsin. For example, as shown in the examples described below, it was confirmed that the degradation of hemoglobin by pepsin is inhibited by the compounds of the present invention.

The present invention is described in detail below with reference to examples, but the invention is not limited to these examples.

EXAMPLE 1

A. Production of Biologically Active Compounds by Culture of *Kitasatosporia kyotoensis*

Pure seed culture of *Kitasatosporia kyotoensis* strain SAM0107 was inoculated in 3 l of a synthetic medium (pH 7.0) comprising glucose, peptone, corn starch, yeast extract, dry yeast and dipotassium phosphate, followed by aerobic culture under agitation in a small fermentor for 24 hours at 28° C., an aeration rate of 3 l/min and a speed of 300 revolutions/min. The pre-culture (two batches in small fermentors) was inoculated in 300 l of the same synthetic medium as that described above, followed by aerobic culture under agitation in a tank for 17 hours at 28° C., an aeration rate of 210 l/min and a speed of 100 revolutions/min.

The culture mixture was centrifuged, and the supernatant (250 l) was adsorbed on a column (25 l) of Diaion HP-20 (Mitsubishi Chemical Industries Co., Ltd.). The column was washed with 100 l of water and then eluted with 150 l of methanol whereby the fractions having antipepsin activity were collected. The active fractions were pooled, concentrated under reduced pressure and then again adsorbed on a column of the same type (4 l) as that described above. This column was washed with 20 l of water and then subjected to elution with 8 l of each of 40%, 60% and 80% methanol.

The fraction eluted with 60% methanol was concentrated under reduced pressure, and the dry residue was dissolved in 50 ml of 50% methanol. The resulting solution was then introduced to a column (55 mm × 2100 mm) of Sephadex LH-20 (Pharmacia Co., Ltd.). Then the eluate was fractionated into fractions of 15 ml each, the enzyme inhibitory activity was eluted in Fraction Nos. 119 to 176. Fraction Nos. 119 to 139 contained compounds I, III and IV and Fraction Nos. 140 to 176 contained compounds V and VI. The fractions (Nos. 119 to 139) eluted from the HP-20 column in the first half were concentrated under reduced pressure, the dry residue was dissolved in 100 ml of 20% methanol and then introduced to a HP-20 column which had previously been equilibrated with 20% methanol. The column was subjected to elution with 600 ml of 20% methanol and then with a linear gradient of 20 to 80% methanol (a total volume of 1200 ml). When the eluate was fractionated into fractions of 10 ml each, enzyme inhibitory activity was recovered in the fractions of 20% methanol (containing compounds III and IV) and in Fraction Nos. 81 to 100 (containing compound I). The fractions containing the compounds III and IV were pooled and again separated on a Sephadex LH-20 column (30 mm × 1710 mm, 50% methanol). Fraction Nos. 80 to 92 from the fractionation of 15 ml each contained the inhibitory activity against the enzyme, which were pooled and then concentrated under reduced pressure. The dry residue was dissolved in 50% methanol and then loaded on column of high performance liquid chromatography (Cosmosil 10C18 packed column, 20 mm × 250 mm). The elution was performed at a flow rate of 2 ml/min. The fractions were collected for each of 0.25 min while being monitored by absorption at 235 nm. 0.1% trifluoroacetic acid (TFA) was used as the solvent for the first 4 minutes and then changed to 0.1% TFA-60% acetonitrile in a linear manner over a time of 20 minutes which was then caused to flow for 10 minutes. As a result, 7 mg of pure compound III and 3 mg of pure compound IV were recovered from Fraction Nos. 34 to 36 and Fraction Nos. 56 to 59, respectively (FIG. 1).

Figure 2:
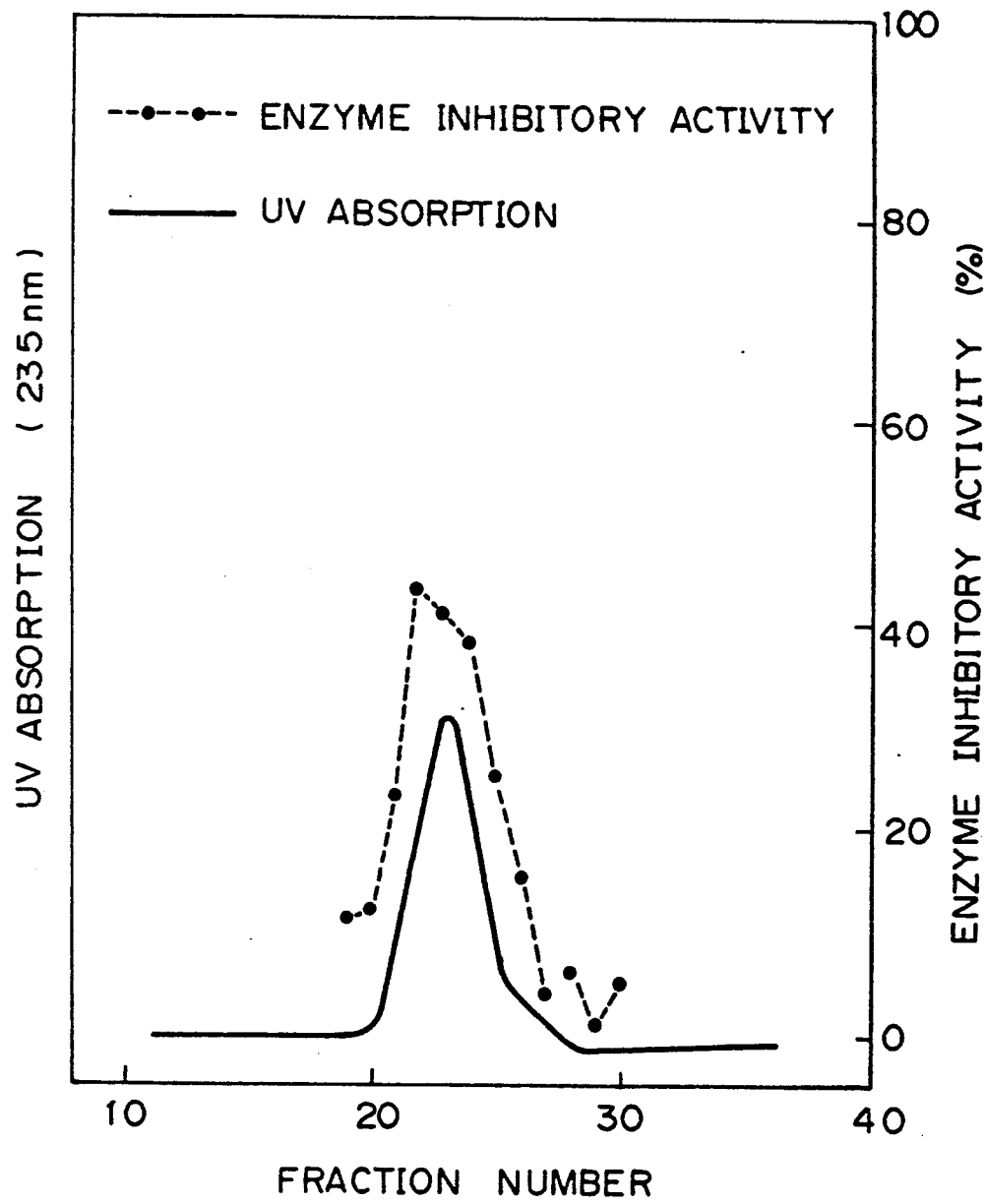
FIG. 2 is a graph of the elution pattern obtained by high performance liquid chromatography in the final stage of production of SUAM-20007.

Fraction Nos. 80–100 from the foregoing sephadex LH-20 column containing the compound I were pooled, concentrated under reduced pressure, the dry residue was dissolved in 90 ml of 30% ethanol and then introduced to a TSKG 3000S (Toyo Soda Co., Ltd.) column (15 mm × 285 mm) which had previously been equilibrated with 30% ethanol. The column was washed with 900 ml of 30% ethanol and then subjected to elution with 50% ethanol. When the eluate was fractionated into fractions of 10 ml each, Fraction Nos. 106 to 123 contained the compound I. These fractions were collected and introduced to a Cosmosil 10C18 packed column as used for the purification of the above-described compounds III and IV. 4 mg of pure compound I was recovered in Fraction Nos. 21 to 25 (FIG. 2).

Figure 3:
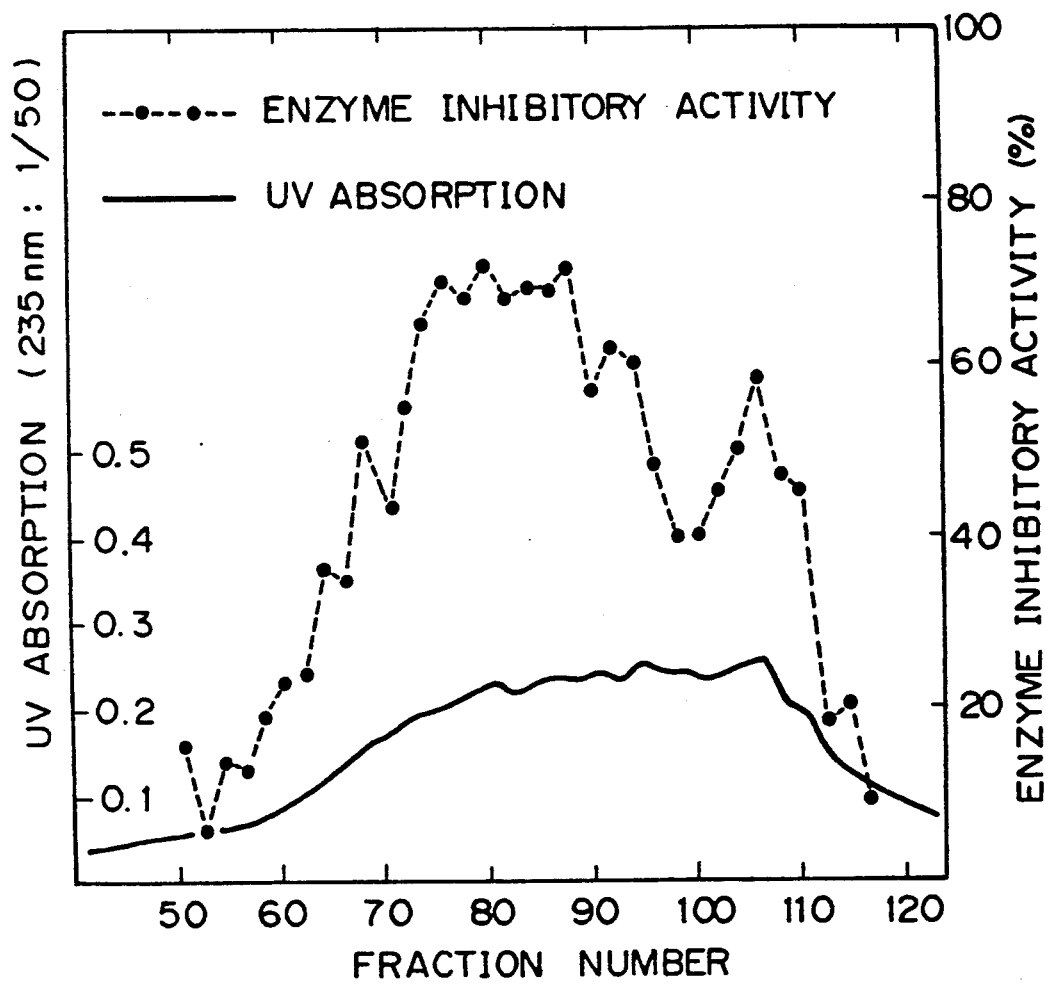
FIG. 3 is a graph of the elution pattern obtained by using a Diaion HP-20 column in production of SUAM-20011 and SUAM-20012.

The fractions (Fraction Nos. 146 to 176) containing the compounds V and VI were concentrated under reduced pressure, the dry residue was dissolved in 100 ml of 20% methanol and then absorbed on a HP-20 column (30 mm × 300 mm) which had previously been equilibrated with 20% methanol. This column was washed with 600 ml of 20% methanol and then subjected to elution using a linear gradient changing from 20 to 80% methanol (a total volume of 1200 l). As a result of fractionation into fractions of 10 ml each, the enzyme inhibitors were recovered in Fraction Nos. 71 to 111 (FIG. 3).

Figure 4:
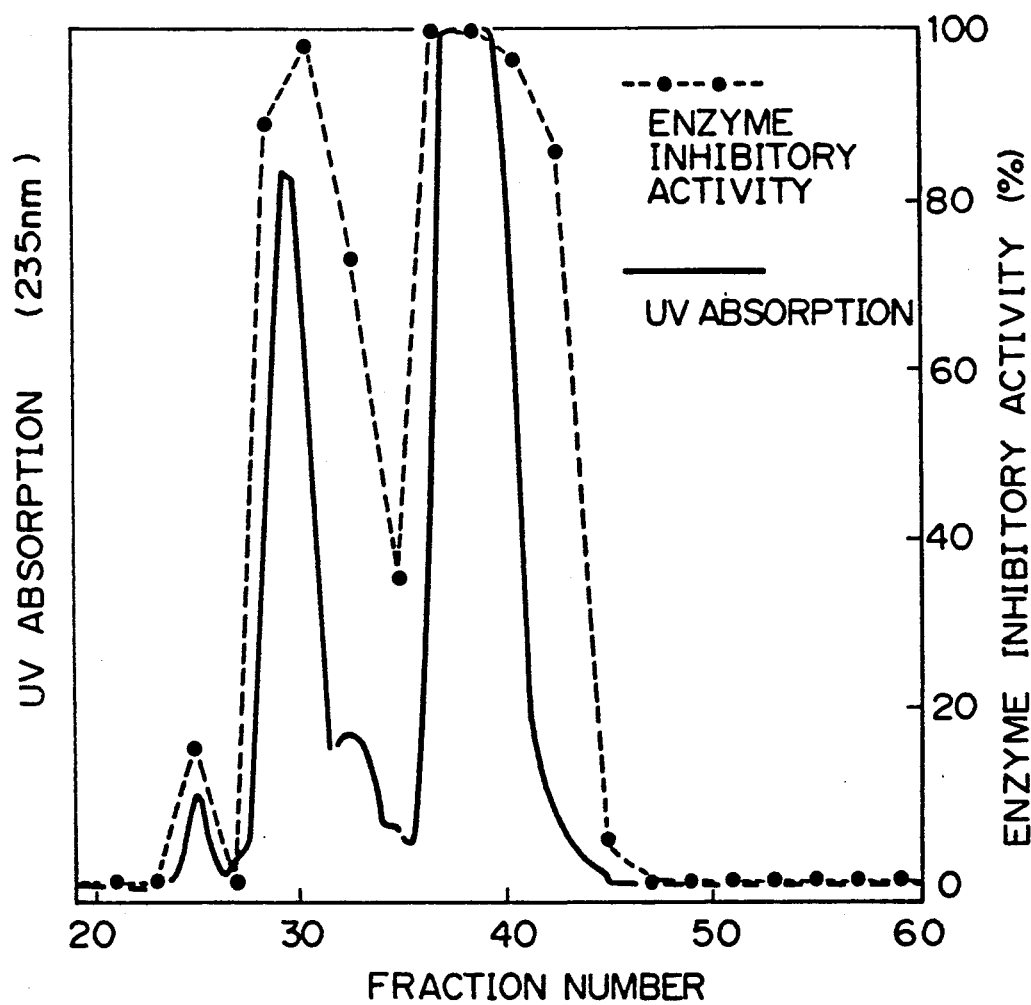
FIG. 4 is a graph of the elution pattern obtained by high performance liquid chromatography in the final stage of production of SUAM-20011 and SUAM-20012.

These active fractions were collected and introduced to a Cosmosil 10C18 packed column in the same way as that described above. 10 mg of pure compound VI and 40 mg of pure compound V were recovered in Fraction Nos. 28 to 31 and 36 to 44, respectively (FIG. 4).

Figure 5:
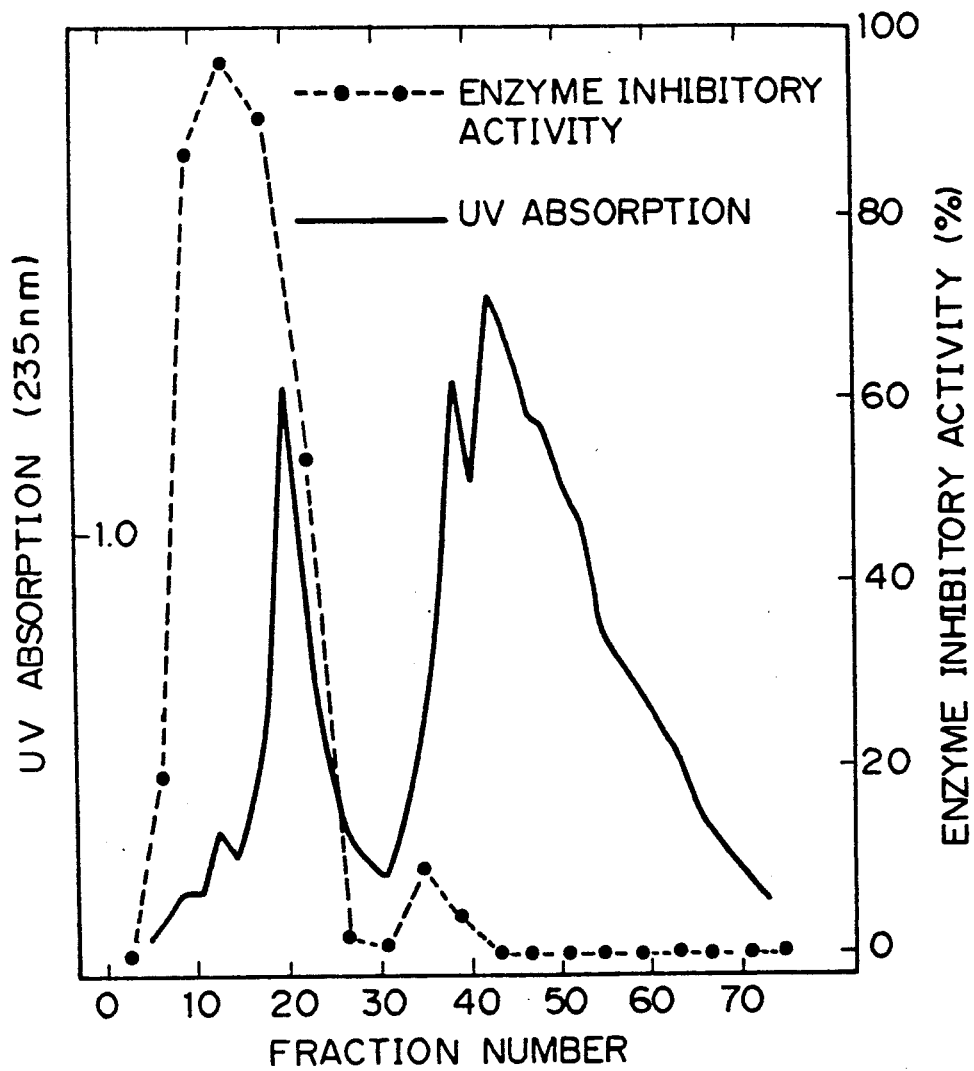
FIG. 5 is a graph of the elution pattern obtained by DEAE cellulose column chromatography in production of SUAM-20008.

The fractions eluted with 80% methanol from the first Diaion column HP-20 were concentrated under reduced pressure, and the dry residue was dissolved in 50 ml of 50% methanol and then passed through a Sephadex LH-20 column (55 mm×2100 mm). As a result of fractionation into fractions of 15 ml each, the enzyme inhibitory activity was eluted in Fraction Nos. 110 to 140. These fractions were concentrated under reduced pressure, and the dry residue was dissolved in 100 ml of 50% methanol. After the pH value of the thus-obtained solution was adjusted to 8, the solution was adsorbed on a DEAE cellulose (Whatman DE23) column (26 mm×110 mm) which had previously been equilibrated with 50% methanol solution in 50 mM ammonium acetate buffer (pH 5.6). As a result of elution by the same solution and fractionation into fractions of 10 ml each, the inhibitory activity was recovered in Fraction Nos. 16 to 18 (FIG. 5).

Figure 6:
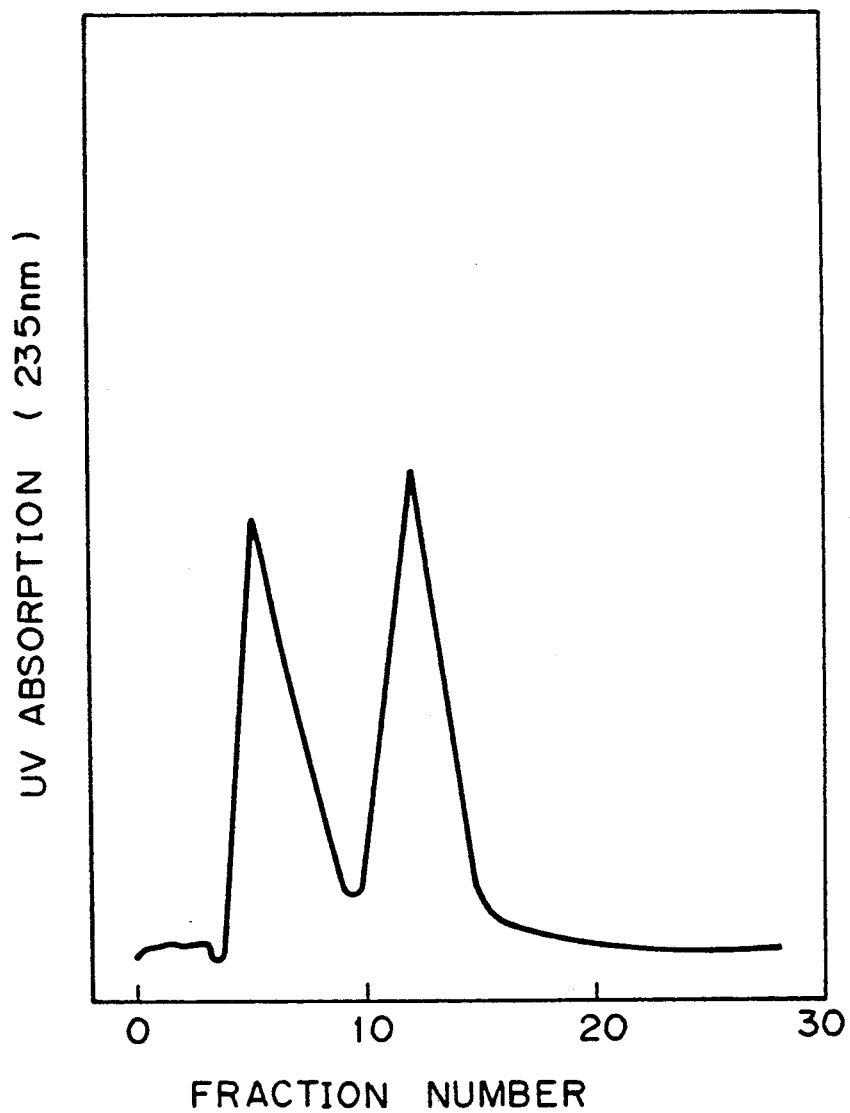
FIG. 6 is a graph of the elution pattern obtained by high performance liquid chromatography in the final stage of production of SUAM-20008.

These active fractions were collected and concentrated under reduced pressure, and the dry residue was dissolved in 50% methanol and then loaded on a packed column for high performance liquid chromatography as described above. As a result, 22 mg of pure compound II was recovered in Fraction Nos. 6 to 10 and 12 to 18 (FIG. 6).

The pure compounds I to VI which were isolated from the culture of *Kitasatosporia kyotoensis* and purified in the above-described steps were respectively named SUAM-20007, SUAM-20008, SUAM-20009, SUAM-20010, SUAM-20011 and SUAM-20012.

B. Physicochemical Properties of the Compounds I-VI (1) Compound I (SUAM-20007)

Form: white powder
Solubility: easily soluble in methanol, ethanol and dimethyl sulfoxide; soluble in butanol; sparingly soluble in water, benzene, ether, petroleum ether, chloroform, carbon tetrachloride, hexane and ethyl acetate
Molecular formula: $C_{44}H_{79}N_7O_{14}$
Molecular weight: 930.1
Mass spectrum: 930 $[M+H]^+$
Proton NMR spectrum: TMS standard
  0.80–1.10 (30H, m), 1.20–1.40 (9H, m), 1.50–1.80 (9H, m), 2.00–2.10 (2H, m), 2.30–2.50 (6H, m), 4.00 (6H, m), 3.65 (1H, q, J=5.0), 4.05–4.20 (2H, m), 4.30–4.50 (2H, m).
Color reaction: negative in ninhydrin reaction, position in the Rydon-Smith reaction and hydrochloric acid-ninhydrin reaction (2) Compound II (SUAM-20008)

Form: white powder
Solubility: easily soluble in methanol, ethanol and dimethyl sulfoxide; soluble in butanol; sparingly soluble in water, benzene, ether, petroleum ether, chloroform, carbon tetrachloride, hexane and ethyl acetate
Molecular formula: $C_{43}H_{77}N_7O_{12}$
Molecular weight: 884.1
Mass spectrum: 884 $[M+H]^+$
proton NMR spectrum: TMS standard
  0.80–1.10 (30H, m), 1.20–1.24 (9H, m), 1.50–1.58 (9H, m), 2.10 (3H, s), 2.00–2.10 (2H, m), 2.30–2.50 (4H, m), 4.00–4.40 (9H, m).
Color reaction: negative in ninhydrin reaction negative, positive in the Rydon-Smith reaction and hydrochloric acidninhydrin reaction (3) Compound III (SUAM-20009)

Form: white powder
Solubility: easily soluble in methanol, ethanol and dimethyl sulfoxide; soluble in butanol; sparingly soluble in water, benzene, ether, petroleum ether, chloroform, carbon tetrachloride, hexane and ethyl acetate
Molecular formula: $C_{34}H_{61}N_5O_{11}$
Molecular weight: 715.9
Mass spectrum: 716 $[M+H]^+$
Proton NMR spectrum: TMS standard
  0.80–0.95 (12H, m), 0.98 (6H, d, J=5.2), 1.02 (6H, d, J=5.2), 1.37 (2H, m), 1.38 (3H, d, J=5.0), 1.40 (3H, d, J=5.0), 1.50–1.70 (4H, m), 2.20 (2H, m), 2.30–2.50 (4H, m), 3.62 (3H, s), 3.63 (1H, q, J=5.0), 4.00 (4H, m), 4.10 (1H, d, J=5.2), 4.18 (1H, d, J=5.2), 4.30 (1H, d, J=5.0)
Color reaction: negative in ninhydrin reaction, positive in Rydon-Smith reaction and hydrochloric acid-ninhydrin reaction (4) Compound IV (SUAM-20010)

Form; white powder
Solubility: easily soluble in methanol, ethanol and dimethyl sulfoxide; soluble in butanol; sparingly soluble in water, benzene, ether, petroleum ether, chloroform, carbon tetrachloride, hexane and ethyl acetate
Molecular formula: $C_{33}H_{59}N_5O_{11}$
Molecular weight: 701.9
Mass spectrum: 702 $[M+H]^+$
Proton NMR spectrum: TMS standard
  0.80–0.95 (12H, m), 0.98 (6H, d, J=5.2), 1.02 (6H, d, J=5.2), 1.35 (2H, m), 1.38 (6H, m), 1.50–1.70 (4H, m), 2.10–2.25 (2H, m), 2.30–2.50 (4H, m), 3.63 (1H, q, J=5.0), 4.00 (4H, m), 4.10 (1H, d, J=5.0), 4.18 (1H, d, J=5.0), 4.30 (1H, d, J=5.0)
Color reaction: negative in ninhydrin reaction, positive in the Rydon-Smith reaction and hydrochloric acid-ninhydrin reaction (5) Compound V (SUAM-20011)

Form: white powder
Solubility: easily soluble in methanol, ethanol and dimethyl sulfoxide; soluble in butanol; sparingly soluble in water, benzene, ether, petroleum ether, chloroform, carbon tetrachloride, hexane and ethyl acetate
Molecular formula: $C_{33}H_{59}N_6O_9$
Molecular weight: 669.9
Mass spectrum: 670 $[M+H]^+$
Proton NMR spectrum: TMS standard
  0.80–1.10 (24H, m), 1.20–1.24 (6H, m), 1.50–1.70 (6H, m), 2.15 (3H, s), 2.00–2.10 (2H, m), 2.30–2.45 (2H, m), 3.63 (3H, s), 3.70 (1H, m), 4.00 (3H, m), 4.10–4.25 (2H, m), 4.25–4.30 (2H, m)
Color reaction: negative in ninhydrin reaction positive in the Rydon-Smith reaction and hydrochloric acid-ninhydrin reaction (6) Compound VI (SUAM-20012)

Form: white powder
Solubility: easily soluble in methanol, ethanol and dimethyl sulfoxide; soluble in butanol; sparingly soluble in water, benzene, ether, petroleum ether, chloroform, carbon tetrachloride, hexane and ethyl acetate Molecular formula: $C_{32}H_{57}N_5O_9$ Molecular weight: 655.8

Mass spectrum: 655 $[M+H]^+$

Proton NMR spectrum: TMS standard 0.80–1.10 (24H, m), 1.20–1.24 (6H, m), 1.50–1.70 (6H, m), 2.00–2.10 (2H, m), 2.30–2.45 (2H, m), 3.63 (3H, s), 3.70 (1H, m), 4.00 (3H, m), 4.10–4.25 (2H, m), 4.25–4.30 (2H, m)

Color reaction; negative in ninhydrin reaction, positive in the Rydon-Smith reaction and hydrochloric acid-ninhydrin reaction The solubility of all of these compounds I–VI in methanol was 10 times as high as that of previously known pepstatin analogues (for example, pepstatin).

C. Analysis of Amino Acids of Compounds I–VI 2 to 3 μg of each of the SUAM-20007, 20008, 20009, 20010, 20011 and 20012 was dissolved in 0.1 ml of 6N-hydrochloric acid, vacuum-sealed in a tube and then hydrolyzed at 105° C. for 48 hours. After hydrolysis, each of the reaction mixtures was dried under vacuum and dissolved in 0.3 ml of 0.02N-hydrochloric acid which was added thereto. A 0.225 ml aliquot of the solution was used in the analysis of amino acids and alanine and valine were thereby detected from all of the compounds. In consideration of the molecular weight and the molar ratio of the constituent amino acids of each of the compounds, the values described in the next table were obtained.

| SUAM No. | Number of valine molecules | Number of alanine molecules |
|---|---|---|
| 20007 | 2 | 2 |
| 20008 | 2 | 2 |
| 20009 | 2 | 1 |
| 20010 | 2 | 1 |
| 20011 | 2 | 1 |
| 20012 | 2 | 1 |

From the results of the aforementioned analysis, the structures of the compounds (SUAM-20007 to 20012) were determined as follows:

(1) Compound I (SUAM-20007)

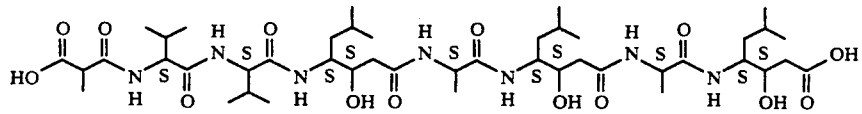

(2) Compound II (SUAM-20008)

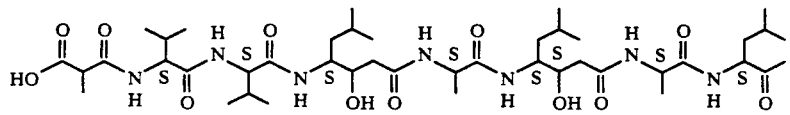

(3) Compound III (SUAM-20009)

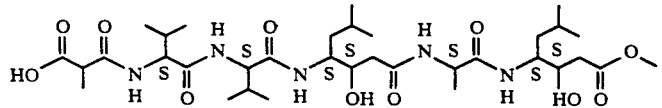

(4) Compound IV (SUAM-20010)

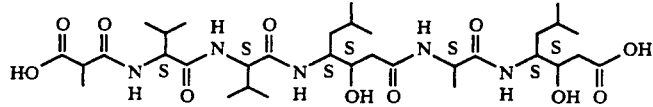

(5) Compound V (SUAM-20011)

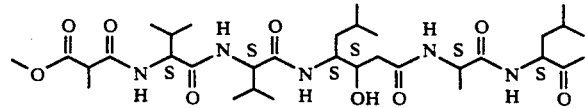

(6) Compound VI (SUAM-20012)

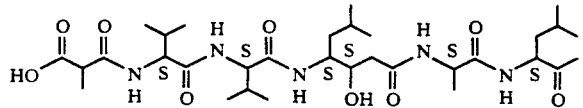

EXAMPLE 2

Enzyme Inhibitory Activity of the Compounds

The enzyme inhibitory activity of each of the compounds SUAM-20007, 20008, 20009, 20010, 20011 and 20012 of the present invention was measured by the following method:

(a) Inhibition against Pepsin from Bovine Pancreas

A given μl aliquot (a μl), which ranged from 0–50 μl, was taken from an aqueous solution of each of the compounds prepared in Example 1 at various set concentrations and was mixed with an aqueous solution of pepsin (50 μg/50 μl). To this mixture was added (150-a) μl of 0.06N-hydrochloric acid to adjust the pH value of the mixture to 3 to 5. Each of the solutions was then mixed with a substrate solution to start the reaction. The substrate for the reaction comprised 2.0% hemoglobin in 800 μl of 0.06N-hydrochloric acid and the reaction was conducted at 35° C. for 10 minutes, the total volume of the reaction mixture being 1 ml. 3 ml of 5% trichloroacetic acid was then added to the reaction mixture to terminate the reaction. After the precipitates formed had been filtered off, the amount of protein in the trichloroacetic acid fraction which contained the components of hemoglobin hydrolyzed with pepsin was measured from the value of ultraviolet absorption at 280 nm. The inhibitory activity which was defined as the concentration of the compound required to achieve 50% inhibition ($IC_{50}$) of each of the compounds was determined by comparison with a control solution. The resulting values obtained were as follows:

| SUAM No. | $IC_{50}$ (M) |
| --- | --- |
| 20007 | $2.91 \times 10^{-8}$ |
| 20008 | $1.42 \times 10^{-8}$ |
| 20009 | $2.24 \times 10^{-8}$ |
| 20010 | $1.43 \times 10^{-8}$ |
| 20011 | $2.54 \times 10^{-8}$ |
| 20012 | $2.60 \times 10^{-8}$ |
| Pepstatin | $1.83 \times 10^{-8}$ |

The biologically active compounds of the present invention have a characteristic structure on the N-terminal side thereof and are highly soluble in solvents (particularly methanol) and thus can be easily purified. Since the compounds also have enzyme inhibitory activity against aspartic proteinases such as pepsin and the like, they will be useful for inhibiting the occurrence of gastric ulcer which is thought to be caused by aspartic proteinase, shortening the time of recovery therefrom, preventing proliferation of granuloma, preventing hepatic hypertension and preventing formation of virus disease lesion. Since the compounds of the present invention can also be used as ligands to form affinity columns, they are useful in application as reagents for purifying aspartic proteinases and for research on the mechanism of enzyme reactions.

What is claimed is:

1. A compound of the general formula I:

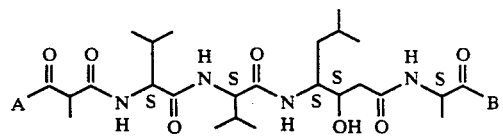

wherein A represents —OH or —O—CH₃ and B represents

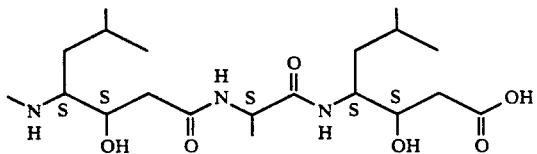

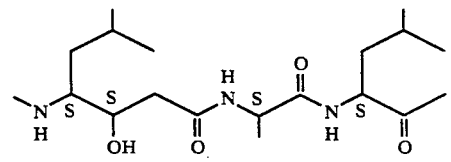

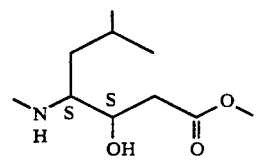

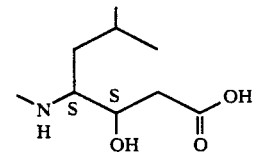

or

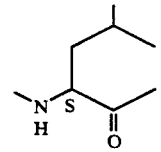

2. A pharmaceutical composition which comprises at least one compound of the general formula I as defined in claim 1, together with a pharmaceutically acceptable carrier.

* * * * *